(12) United States Patent
Weiss

(10) Patent No.: US 6,676,694 B1
(45) Date of Patent: Jan. 13, 2004

(54) METHOD FOR INSTALLING A STENT GRAFT

(76) Inventor: Mitchell Weiss, 300 Pinellas St. Radiology Dept. MS-35, Clearwater, FL (US) 33756

(*) Notice: Subject to any disclaimer, the term of this patent is extended or adjusted under 35 U.S.C. 154(b) by 0 days.

(21) Appl. No.: 10/064,070

(22) Filed: Jun. 6, 2002

(51) Int. Cl.⁷ .................................................. A61F 2/06
(52) U.S. Cl. ........................ 623/1.11; 623/902; 623/903; 623/909; 606/108; 606/194
(58) Field of Search ................................ 606/108, 194; 623/1.11, 902, 903, 909

(56) References Cited

U.S. PATENT DOCUMENTS

| | | | | |
|---|---|---|---|---|
| 5,380,270 A | * | 1/1995 | Ahmadzadeh | 604/9 |
| 6,258,098 B1 | * | 7/2001 | Taylor et al. | 606/108 |
| 6,264,662 B1 | * | 7/2001 | Lauterjung | 606/108 |

* cited by examiner

Primary Examiner—Corrine McDermott
Assistant Examiner—Kamrin Landrem
(74) Attorney, Agent, or Firm—Ronald E. Smith; Smith & Hopen, P.A.

(57) ABSTRACT

A first catheter has a return bend formed near its distal free end and a first magnet is mounted on the distal free end. The first catheter is introduced through a sheath in a first common femoral artery into an elongate leg of a stent graft and pulled back until the return bend positions the first magnet near a truncate leg of the stent graft. A second catheter having a second magnet on its distal free end is introduced through a second common femoral artery and positioned near the first magnet so that the magnets become interconnected. The second catheter is pulled into the stent graft, a guide wire is inserted through it, and a second sheath is introduced into the stent graft. A contralateral limb is deployed through the second sheath and the second sheath is removed. In another embodiment, catheters with magnets pull a nephroureteral stent from a kidney.

5 Claims, 11 Drawing Sheets

METHOD FOR INSTALLING A STENT GRAFT

BACKGROUND OF INVENTION

1. Field of the invention

This invention relates, generally, to the medical arts. More particularly, it relates to a method for endoluminal installation of a stent graft.

2. Description of the prior art

Stent grafts are used to hold arteries open so that blood may flow therethrough. They also have utility in treating aneurysms, in effect replacing an artery where the walls of the artery have ballooned outwardly and are in danger of rupturing. Stent grafts are formed of materials that are inert to the human body so that they may be left in place indefinitely. The materials from which stent grafts are made are highly flexible so that they may be compressed into a small space such as a lumen of a catheter. The materials are also highly resilient, i.e., have excellent memory, so that when a stent graft is pushed out of the lumen of a catheter, it expands under its inherent bias to its operable size.

Tubular stent grafts are relatively easy to deploy in straight sections of arteries. However, there are areas of the body where deployment is problematic because a tubular stent graft cannot be used. A section of the abdominal artery, just slightly upstream of where it divides into the left and right iliac arteries, also known as the left and right common iliac arteries, is prone to the development of aneurysms and is a location where a tubular stent graft has no utility.

The stent graft that has been developed for this problematic area of the abdominal artery is often described as looking like a pair of pants having a waist part with one long leg and one short leg depending therefrom. When properly deployed, the waist part and the short leg thereof are positioned within the aneurysm of the abdominal artery, just downstream of the renal arteries. The long leg has a trailing end disposed within a first common iliac artery. If the short leg were also elongate and if its trailing end could easily be fitted into the second common iliac artery, then the positioning of a stent graft in an abdominal artery aneurysm would not be problematic.

Deploying a stent graft in an abdominal artery aneurysm so that blood can flow through the stent graft and avoid putting pressure on the ballooned arterial walls is difficult because the waist part of the stent graft must be positioned within the abdominal artery, and the left and right legs of the stent graft must fit into the left and right common iliac arteries, respectively.

There are two basic designs for endoluminal stents having utility in the repair of abdominal aortic aneurysms. Two. elongate legs are provided in the first design. A first leg is positioned in the first iliac artery and a second leg is pulled into the second iliac artery to form an inverted "Y" configuration. The present invention pertains to the second design where the stent includes a long leg and a short leg. An extension for the short leg is manufactured as a separate piece and is known as a contralateral limb because it is laterally opposed with respect to the first elongate leg of the stent graft. The physician inserts the contralateral limb into the short leg, thereby creating a conduit from the stent to the contralateral iliac artery and excluding blood flow from the aneuryismaneurysm.

Thus, in the second design, an extension for the short leg must be manufactured as a separate piece, and the physician must insert the extension for the short leg into the second iliac artery and try to secure it to the short leg.

The method most commonly employed to join a contralateral limb to the short leg of a stent graft is to introduce the contralateral limb through an incision in the patient's leg-groin. More particularly, the contralateral limb is endoluminally introduced through a common femoral artery. The leading end of the contralateral limb is inserted into the trailing end of the short leg of the stent graft and the trailing end of the contralateral limb is left in the second common iliac artery to complete the installation.

There are several drawbacks to this approach, but the primary drawback is that it requires a physician to correctly aim the leading end of the contralateral limb at the trailing end of the stent graft short leg. This is a very difficult task under fluoroscopy or other imaging technique. What might look like a perfect connection may be a complete miss. For example, if the leading end of the contralateral limb goes directly underneath the trailing end of the short leg of the stent graft, it will appear to the physician performing the procedure that the alignment is perfect and that the job has been successfully completed. The results of such a misalignment are catastrophic.

What is needed, then, is an improved method for endoluminally introducing the leading end of a contralateral limb into the trailing end of the short leg of a stent graft.

However, in view of the prior art considered as a whole at the time the present invention was made, it was not obvious to those of ordinary skill in the pertinent art how such need could be fulfilled.

SUMMARY OF INVENTION

The long-standing but heretofore unfulfilled need for an improved method for installing a contralateral limb to a stent graft in the area of an abdominal artery aneurysm is now met by a new, useful, and nonobvious invention. The novel method includes the steps of inserting a first guide wire through an incision endoluminally into a first common femoral artery and pushing the first guide wire into the abdominal artery until a leading end of the first guide wire extends beyond a leading end of the stent graft. A first sheath is endoluminally introduced into an elongate leg of the stent graft, using the first guide wire to guide the first sheath into the elongate leg. The elongate leg has a trailing end received within the first iliac artery. The first guide wire is then removed from the sheath. A first catheter having a return bend formed near its distal end and having a first magnet means mounted to the distal end is introduced into a lumen of the first sheath. The first catheter is pushed into the first sheath until the return bend emerges from the lumen of said first sheath. The first catheter is then displaced in a distal-to-proximal direction, relative to the incision site, until the first magnet means emerges from the hollow interior of the stent graft and into the interior of the aneurysm. A second catheter having a second magnet means on a distal free end thereof is introduced into a second, opposite femoral artery and positioned near the first magnet means so that the first and second magnet means (having a polarity opposite to that of the first) are attracted to one another. The second catheter is then pulled into the hollow interior of the stent graft. A second guide wire is then introduced into the lumen of the second catheter until the distal free end of the second guide wire has extended completely through the second catheter and through the stent graft. The first and second catheters are then removed. A second sheath is introduced over the second guide wire until the distal free end of the second sheath has entered the hollow interior of the stent graft. A contralateral limb is then introduced through the second sheath until the distal free end of the contralateral limb has extended from the second sheath and entered into the hollow interior of the stent graft. The contralateral limb deploys under its inherent bias so that it expands in diameter. The second sheath is then withdrawn and blood flows into a first end of the. stent graft and out the bifurcated lower end thereof into the left and right iliac arteries.

The steps of the novel method may also be performed with a modified version of the first catheter. An opening is formed in the distal end of the first catheter in close proximity to the first magnet means secured to the distal end of the first catheter. The opening may also be formed in close proximity to the reverse bend formed in the first catheter. A guide wire extends through the first catheter from its proximal end and exits through the opening. This configuration minimizes the profile of the first catheter by placing the magnet therewithin instead of on the outside of the first catheter and thus dedicates the lumen of the first catheter to the guide wire. Moreover, the guide wire provides additional support for pushing the catheter cephalad beyond the leading end of the stent graft. After the catheter is advanced over the guide wire, the guide wire is withdrawn into the straight part of the first catheter proximal to the reverse bend or the guide wire is completely removed from the lumen.

The step of removing the first and second catheters is accomplished by pulling on the second catheter until the magnetic coupling between the first and second magnet means is overcome.

In an alternative embodiment, an opening is formed in a first straight-in-configuration catheter near its distal end. A pull string extends through the first catheter from its proximal end and exits the first catheter through said opening. The distal end of the pull string is secured to a first magnet means mounted on the distal end of the first catheter, or to the catheter in very close proximity to the first magnet. Pulling on the pull string thus forms a return bend in the distal end of the first catheter and positions the first magnet to a position where it can be more easily connected to a second magnet at the second end of a second catheter that is introduced through the contralateral limb.

In another alternative embodiment, a magnetic band having a polarity opposite to that of the magnet secured to the distal end of a first catheter is secured to the distal end of a second sheath. This eliminates the need for a second catheter. After the magnets have been coupled to one another, the sheath is pulled and pushed into the hollow interior of the stent graft. A deployment system is then employed to facilitate introduction of the contralateral limb through the second sheath. This eliminates the need for a second guide catheter, thereby shortening procedure time.

In another application of the invention, a nephroureteral stent is removed from a kidney by mounting a first magnet or ferromagnetic means to a first end of a nephroureteral stent that extends from a bladder to a kidney through a ureter. A second magnet means having a polarity opposite to a polarity of the first magnet means is mounted on the distal free end of a catheter and the distal free end of the catheter is introduced into the bladder through the urethra. The second magnet means is brought into close proximity with the first magnet means so that the first and second magnet means enter into a magnetic coupling with one another. The catheter is then withdrawn through the urethra, thereby pulling the first magnet means and hence the nephroureteral stent with it.

An alternative embodiment of the invention comprises the addition steps of threading a pull string through said catheter, said pull string having a first end and a second end, establishing a string aperture proximate to said first magnet, securing said first end to said catheter coincident to said first magnet whereby retraction of said second end draws said first magnet toward said string aperture thereby forming said return bend.

In all embodiments, one of the magnet means may be provided in the form of a ferrous material that is secured to the distal end of its catheter. For example, a ferrous metal band may be strapped onto the end of a catheter.

The primary object of this invention is to provide a method whereby a contralateral limb is attached to the short leg of a stent graft without requiring a physician to visually guide the contralateral limb into the short leg.

A closely related object is to provide a method that harnesses magnetism to facilitate the steps of the-method.

These and other important objects, advantages, and features of the invention will become clear as this description proceeds.

The invention accordingly comprises the features of construction, combination of elements, and arrangement of parts that-will be exemplified in the description set forth hereinafter and the scope of the invention will be indicated in the claims.

BRIEF DESCRIPTION OF DRAWINGS

For a fuller understanding of the nature and objects of the invention, reference should be made to the following detailed description, taken in connection with the accompanying drawings, in which:

FIG. 14 is the fourteenth animation in said series;

DETAILED DESCRIPTION

Figure 1:
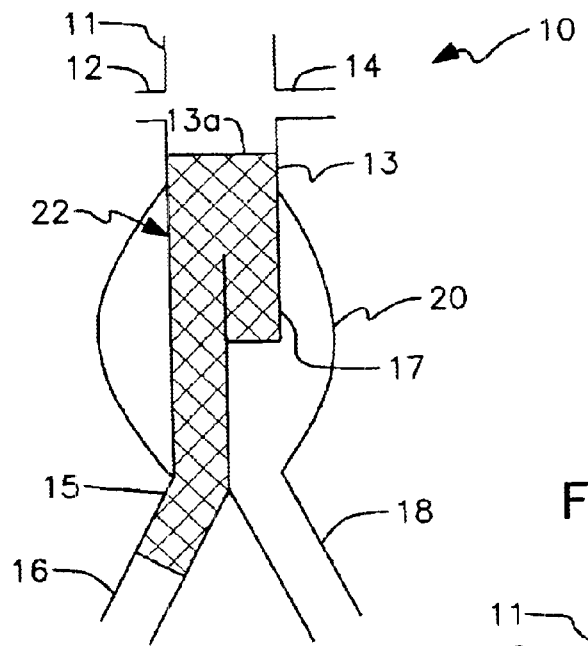
FIG. 1 is a diagrammatic view of a stent graft deployed in an aneurysm.

Referring to FIG. 1, it will there be seen that the reference numeral 10 denotes an aneurysm site in an abdominal artery 11. The renal arteries are denoted 12, 14, the left and right common iliac arteries are denoted 16, 18, respectively, and an aneurysm therebetween is denoted 20. A stent graft is denoted 22 as a whole and is of conventional construction. It has a body or waist area 13 as depicted, an elongate leg 15, and a truncate leg 17. The leading edge of the stent graft is denoted 13a.

Aneurysm 20 is formed in abdominal artery 11 which extends from the aortic opening in the diaphragm, not shown, to a termination point near the fourth lumbar vertebra, not shown, where it divides into the right common iliac artery 16 and the left common iliac artery 18, respectively.

Note in FIG. 1 that a trailing end of elongate leg 15 is positioned within right common iliac artery 16. No such elongate leg can be provided for left common iliac artery 18 as a part of the original construction of stent graft 22 because there are no means for positioning a trailing end of a second elongate leg within said left common iliac artery 18.

The method for installing stent graft 22 in the position depicted in FIG. 1 is well-known and forms no part of this invention, per se. Fluoroscopy or other suitable imaging technique is employed to enable the physician to position the stent graft in its FIG. 1 position. A suitable imaging technique is employed throughout the various steps of the novel method.

Figure 2:
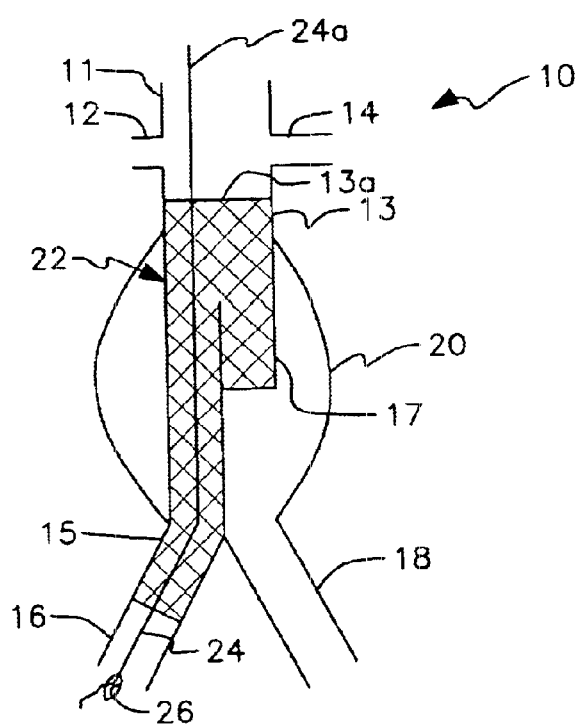
FIG. 2 is the first animation in a series of fourteen animations that depict the steps of the novel method in sequence.

The first step of the novel method is depicted in FIG. 2. Guide wire 24 is endoluminally inserted through incision 26 into the left or ipsilateral common femoral artery 16 and fed through said artery until the distal end 24a of said guide wire is beyond renal arteries 12, 14. Incision 26 is the same incision through which stent graft 22 is inserted prior to commencement of the novel method.

Figure 3:
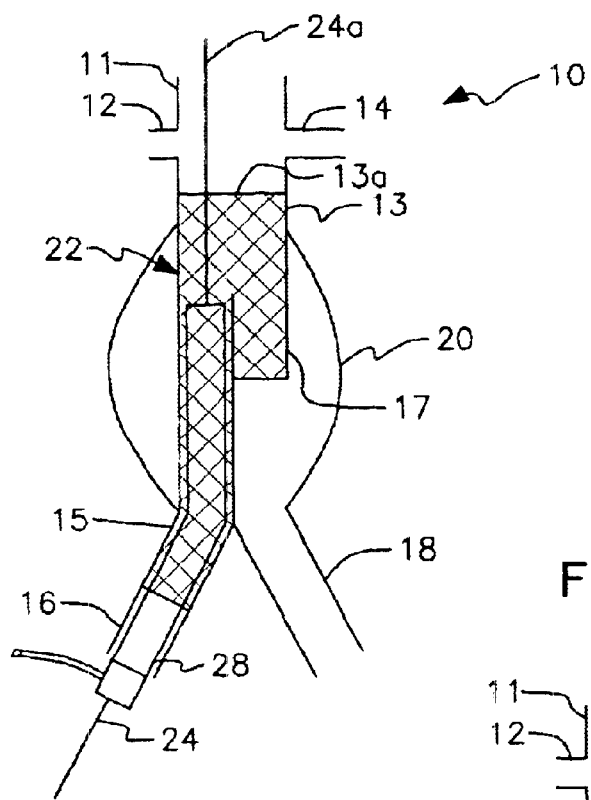
FIG. 3 is the second animation in said series.
Figure 4:
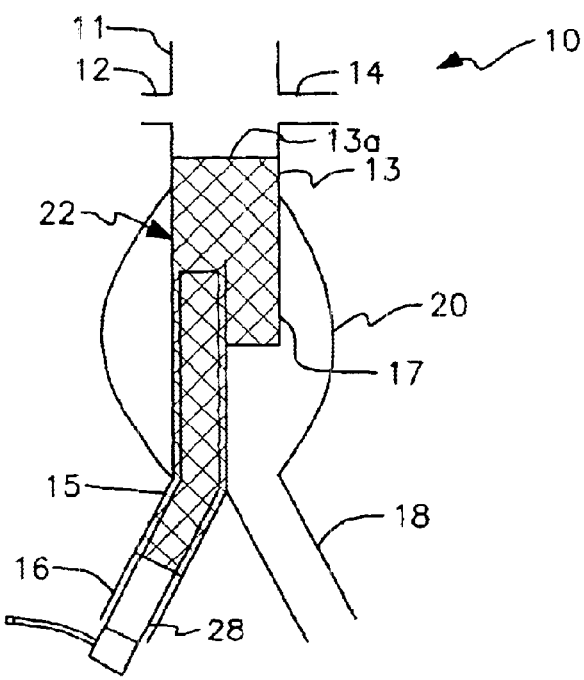
FIG. 4 is the third animation in said series.
Figure 5:
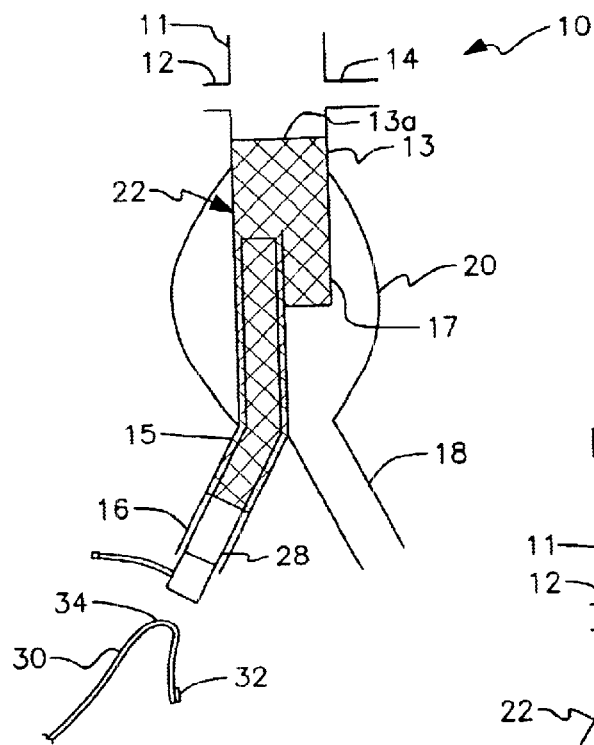
FIG. 5 is the fourth animation in said series.

As depicted in FIG. 3, sheath 28 is then advanced into the ipsilateral side of stent graft 22, using guide wire 24 as a guide means. Guide wire 24 is then removed, leaving sheath 28 in place as depicted in FIG. 4.

FIG., 5 depicts first catheter 30 having magnet 32 at its distal free end. A return bend 34 is pre-formed in said first catheter 30, near said distal free end.

Figure 6:
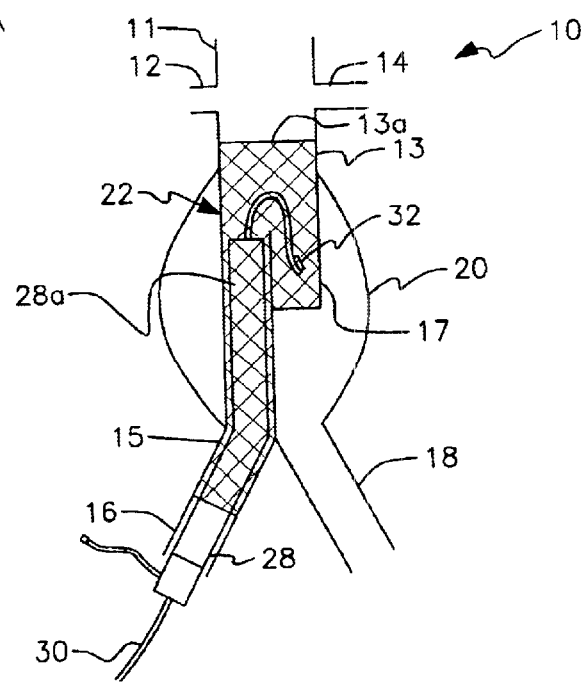
FIG. 6 is the fifth animation in said series.

First catheter 30 is inserted into sheath 28 until magnet 32 and return bend 34 have emerged from the distal free end 28a of sheath 28 as depicted in FIG. 6. Note that first magnet 32 is positioned interiorly of stent graft 22 at this step of the method.

Figure 7:
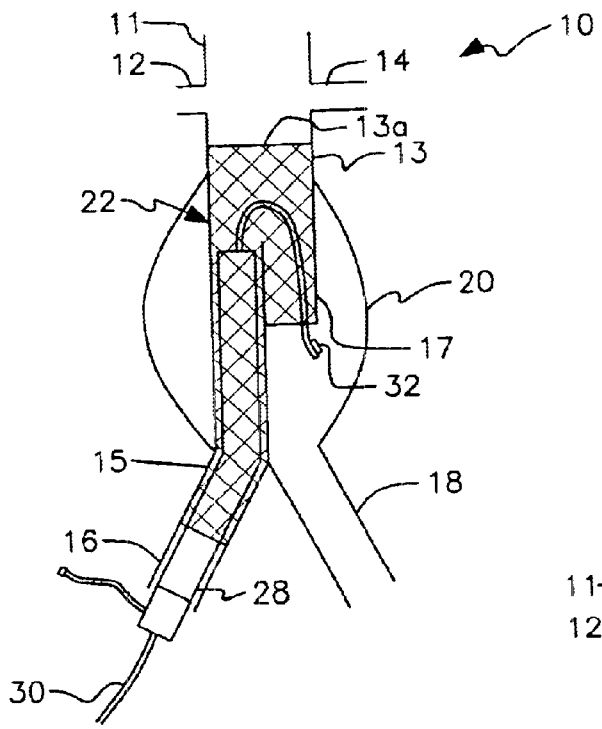
FIG. 7 is the sixth animation in said series.

First catheter 30 is then pulled rearwardly, i.e., in a distal-to-proximal direction, relative to the incision site, until first magnet 32 emerges from the interior of stent graft 22 into the interior of aneurysm 20 as depicted in FIG. 7.

Figure 8:
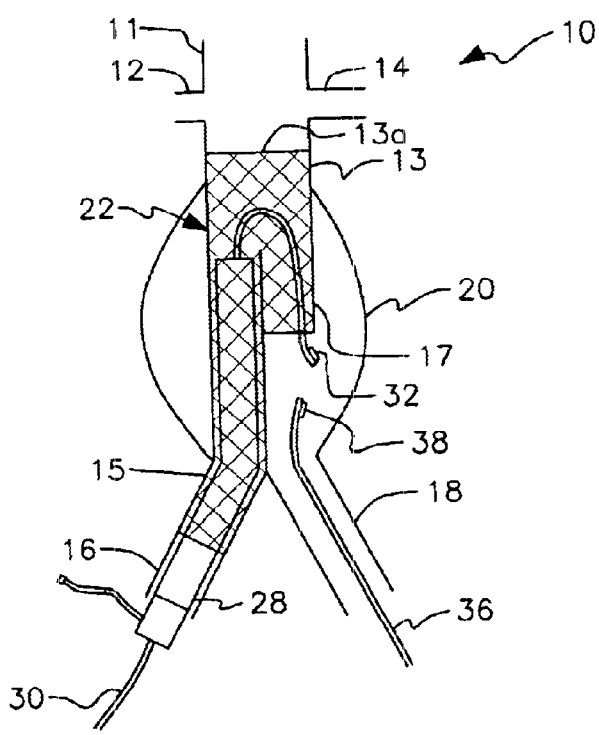
FIG. 8 is the seventh animation in said series.

A second catheter 36 (FIG. 8) is then introduced into the opposite femoral artery 18. Second magnet 38 secured to the distal free end of second catheter 36 has a polarity opposite to the polarity of first magnet 32 so that said magnets 32 and 38 are attracted to one another. Alternatively, one of the magnets could be made of a non-magnetized ferrous material.

Figure 9:
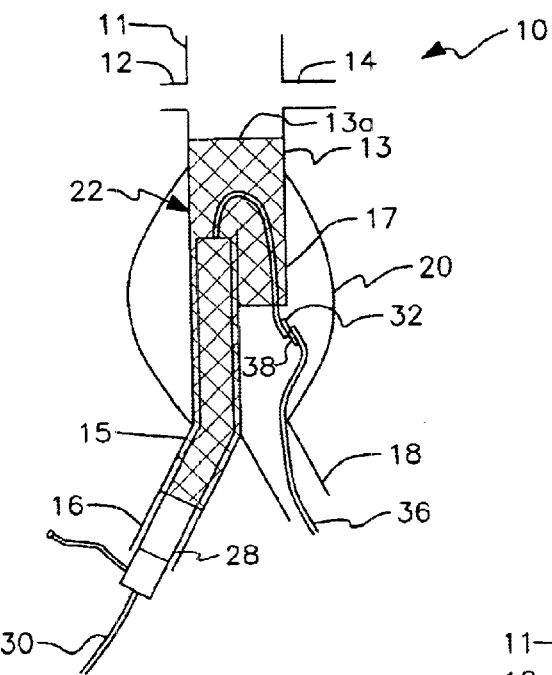
FIG. 9 is the eighth animation in said series.

As indicated in FIG. 9, second catheter 36 is advanced until the magnets are in close proximity to one another, at which time they attract one another and become interconnected.

Figure 10:
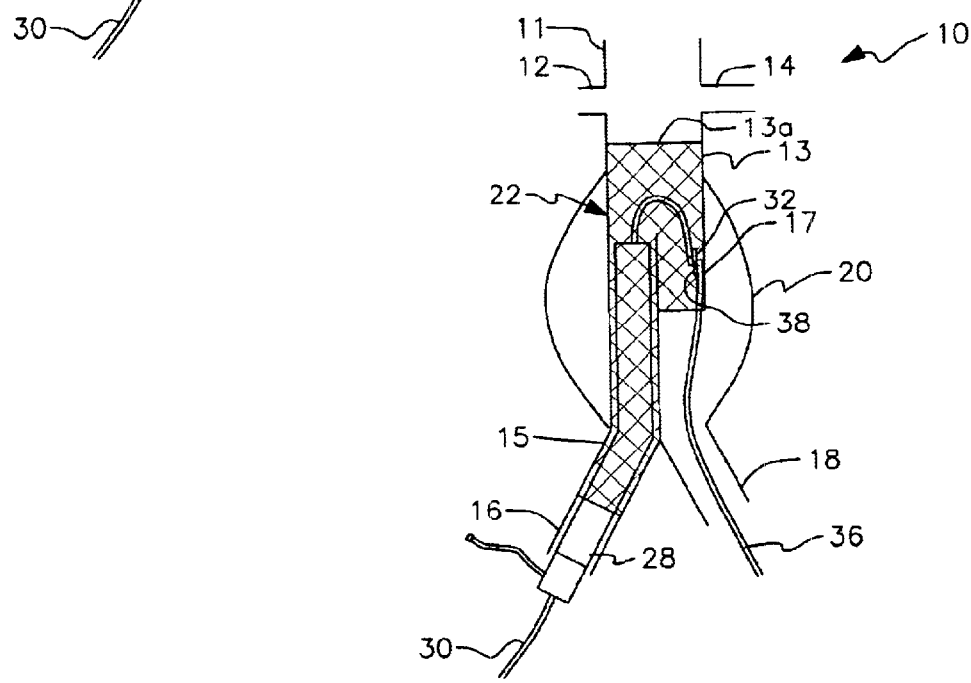
FIG. 10 is the ninth animation in said series.

As depicted in FIG. 10, second catheter 36 is then pulled into the hollow interior of stent graft 22. This may be accomplished by pushing on both catheters 30, 36 simultaneously.

Figure 11:
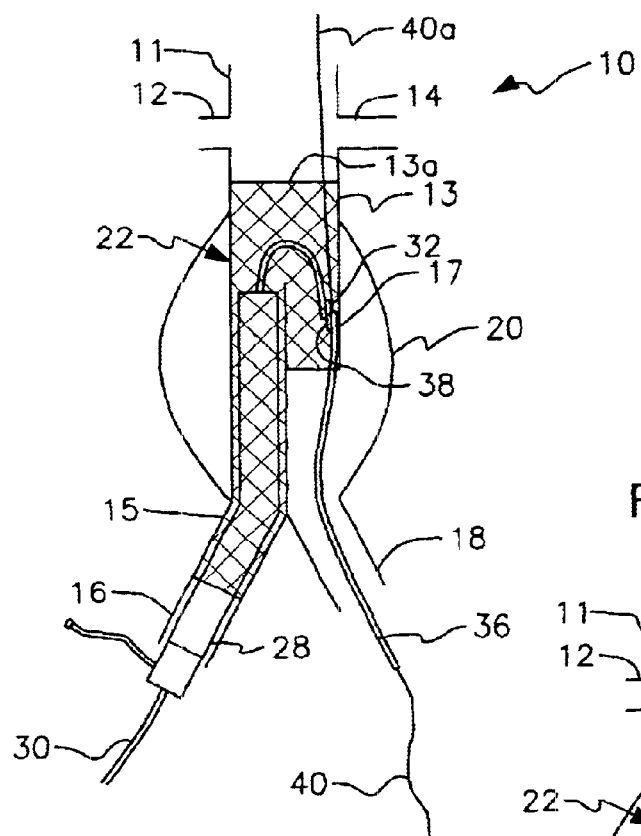
FIG. 11 is the tenth animation in said series.

A second guide wire 40 is then introduced into the lumen of second catheter 36 until its distal free end 40a has extended completely through second catheter 36 and through stent graft 22 as depicted in FIG. 11. Note that this positioning of second guide wire 40 is made possible because the distal free end 36a of second catheter 36 is disposed in the hollow interior of stent graph 22, and said positioning is made possible by the magnetic coupling of magnets 32 and 38.

Figure 12:
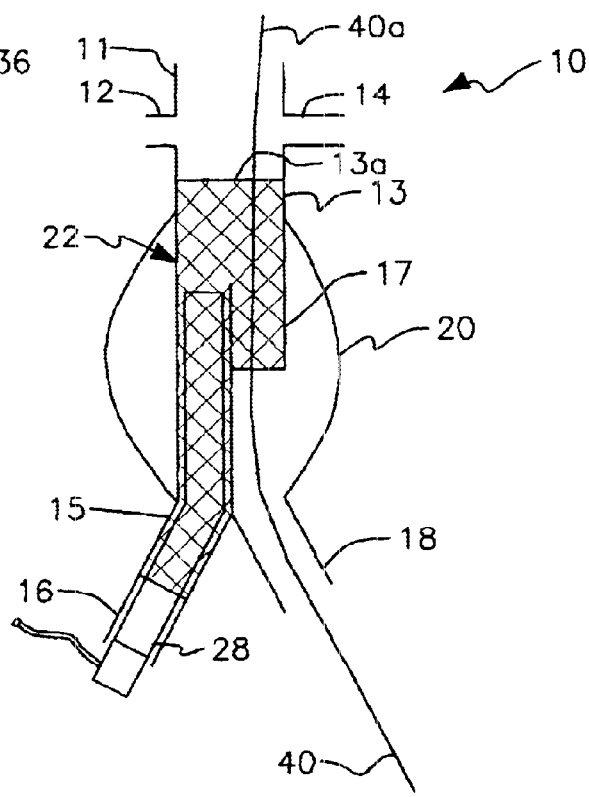
FIG. 12 is the eleventh animation in said series.

First and second catheters 30 and 36 are then removed as indicated in FIG. 12. This may be accomplished by pulling on second catheter 36 until the magnetic coupling between magnets 32 and 38 is overcome, followed by retraction of said first and second catheters.

Significantly, guide wire 40 as depicted in FIG. 12 has been placed with confidence into short leg 17 of stent graft 22.

Figure 13:
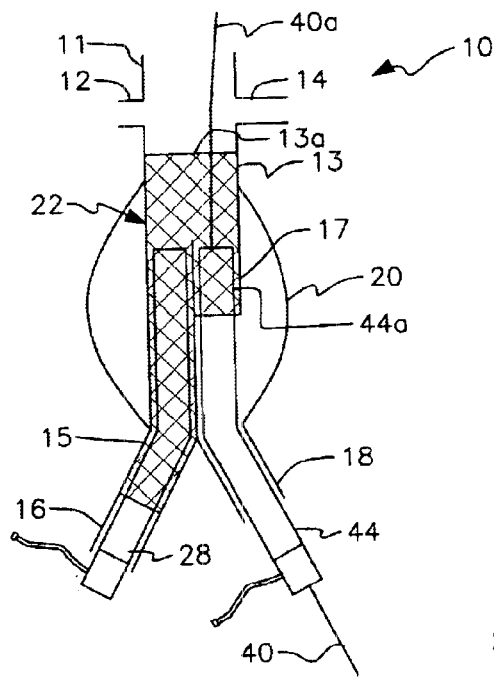
FIG. 13 is the twelfth animation in said series.

Guide wire 40 is then used to guide second sheath 44 until its distal free end 44a has entered the hollow interior of stent graft 22 as depicted in FIG. 13.

Figure 14:
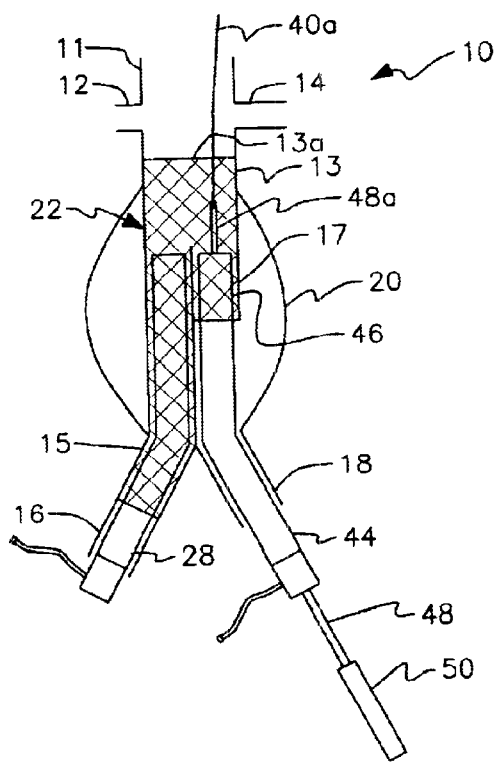
FIG. 14 is the thirteenth animation in said series.

Contralateral limb 48 is then introduced through second sheath 44 until its distal free end 48a has extended from said second sheath and entered into the hollow interior of stent graft 22 as depicted in FIG. 14. Deployment system 50 is employed to facilitate introduction of said contralateral limb 48 through said second sheath 44.

Figure 15:
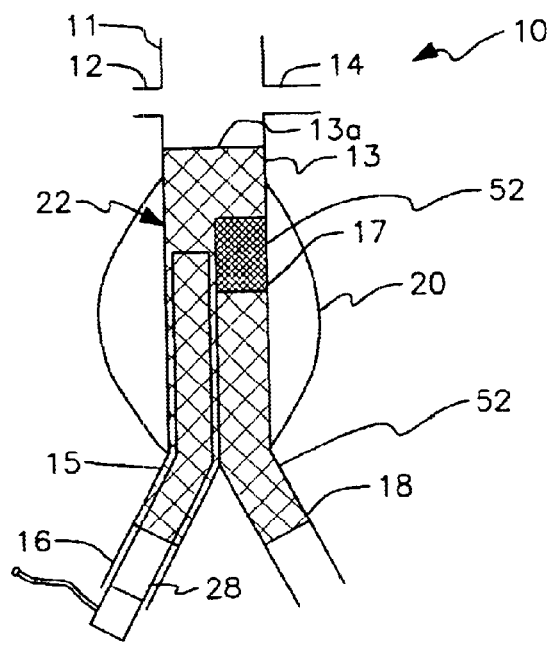
FIG. 15 is the fourteenth animation in said series.

Contralateral limb 48 is then deployed so that it expands in diameter as indicated by the reference numeral 52 in FIG. 15. Second sheath 44 is then withdrawn and the procedure is completed. Blood now flows into the upper end 13a of stent graft 22 and out the bifurcated lower end thereof into arteries 16 and 18. Thus, there is no blood pressure on the ballooned walls of aneurysm 20 and there is no affect on the health of the patient if said walls fail completely.

Figure 15A:
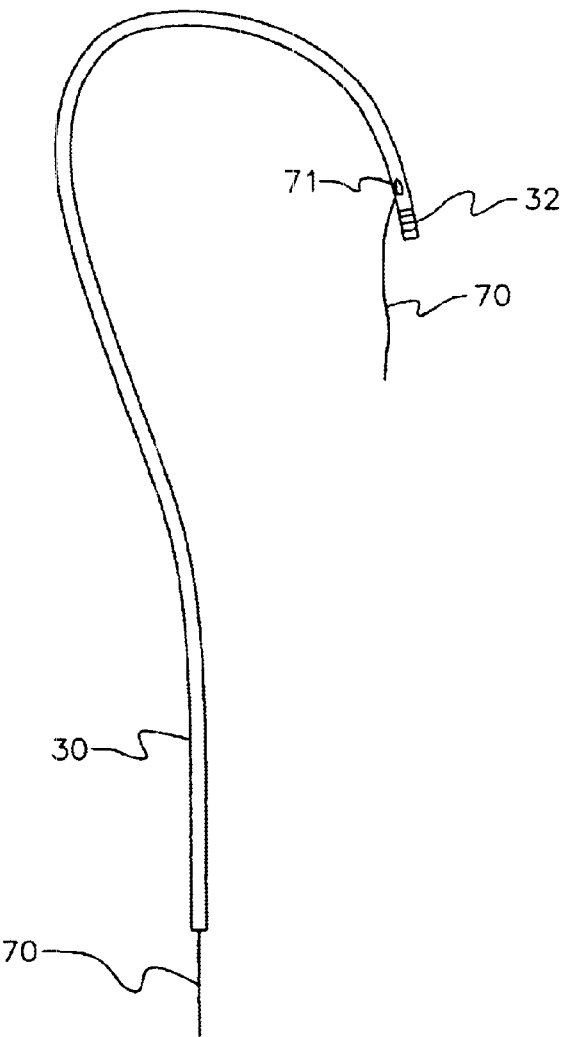
FIG. 15A is a diagrammatic view of an alternative of the first catheter used in the novel method.

The steps of the novel method may also be performed with a modified version of the first catheter. As illustrated in FIG. 15A, an opening is formed in the distal end of the first catheter in close proximity to the first magnet means secured to the distal end of the first catheter. The opening may also be formed in close proximity to the reverse bend formed in the first catheter. A guide wire extends through the first catheter from its proximal end and exits through said opening. This configuration minimizes the profile of the first catheter by placing the magnet therewithin instead of on the outside of the first catheter and thus receives the lumen of the first catheter for the guide wire. Moreover, the guide wire provides additional support for pushing the catheter cephalad beyond the leading end of the stent graft. After the catheter is advanced over the guide wire, the guide wire is withdrawn into the straight part of the first catheter proximal to said reverse bend or said guide wire is completely removed from said lumen. The steps described in connection with FIGS. 6–15 are unchanged when the modified version of the first catheter is used.

Figure 15B:
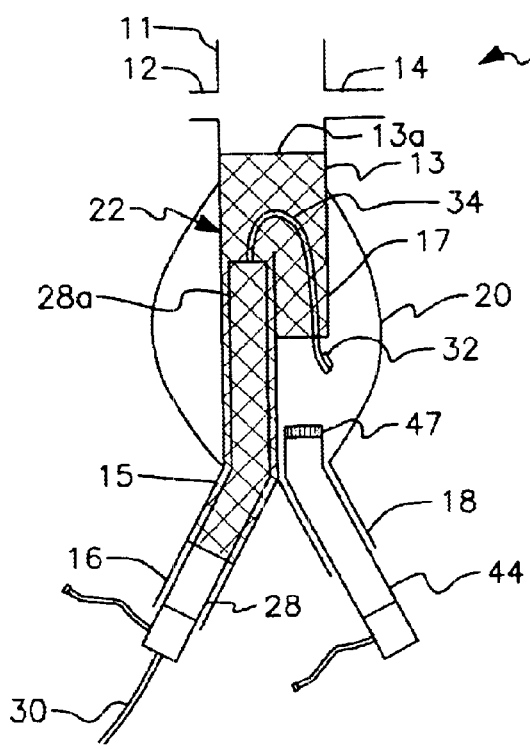
FIG. 15B is a diagrammatic view of a second embodiment.

In a second embodiment, depicted in FIG. 15B, a magnetic band 47 is secured to the distal end of second sheath 44. Magnetic band 47 has a polarity opposite to that of magnet 32 secured to the distal end of catheter 30. This eliminates the need for second catheter 36. After magnets 32 and 47 have been coupled to one another, sheath 44 is pulled and pushed into the hollow interior of stent graft 22 in much the same way as magnets 32 and 38 in FIG. 10. Deployment system 50 (FIG. 14) is then employed to facilitate introduction of said contralateral limb 48 through said second sheath 44. This eliminates the need for guide wire 40.

The methods disclosed herein have been in the context of stent graft deployment, and have resulted in securing access from a first femoral artery to a second femoral artery. In additional embodiments of this invention, the same methods disclosed herein could be used to secure access between two separate points in the vascular, biliary, genito-urinary, or gastrointestinal system. Such "through and through" access is at times beneficial in performing procedures such as balloon angioplasty of very tight strictures. After the catheters are coupled, a wire may be passed from either point of access. The "through and through" access provided by the wire provides the operator greater control by creation of a monorail secured at two ends.

Figure 16:
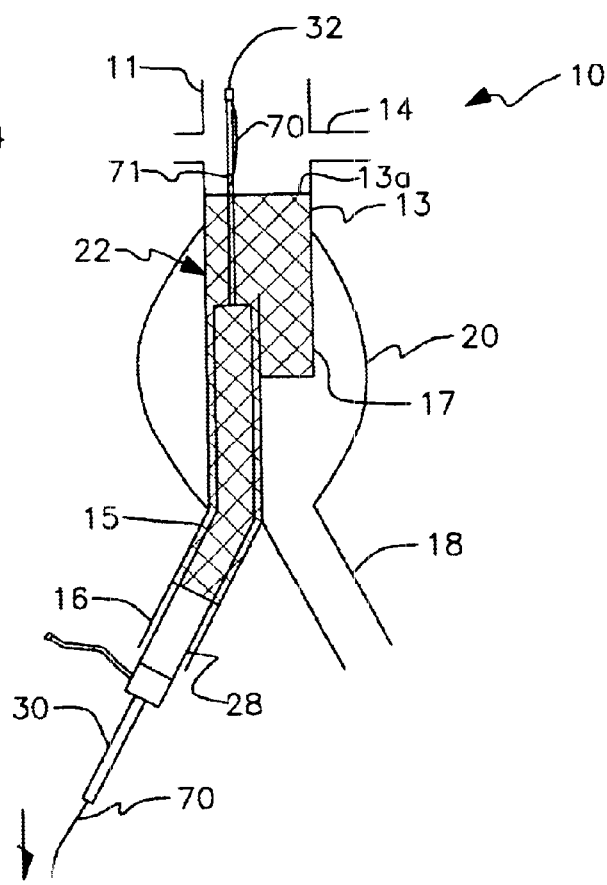
FIG. 16 is the first animation in a series of three animations that depicts the steps of a third embodiment of the invention.
Figure 17:
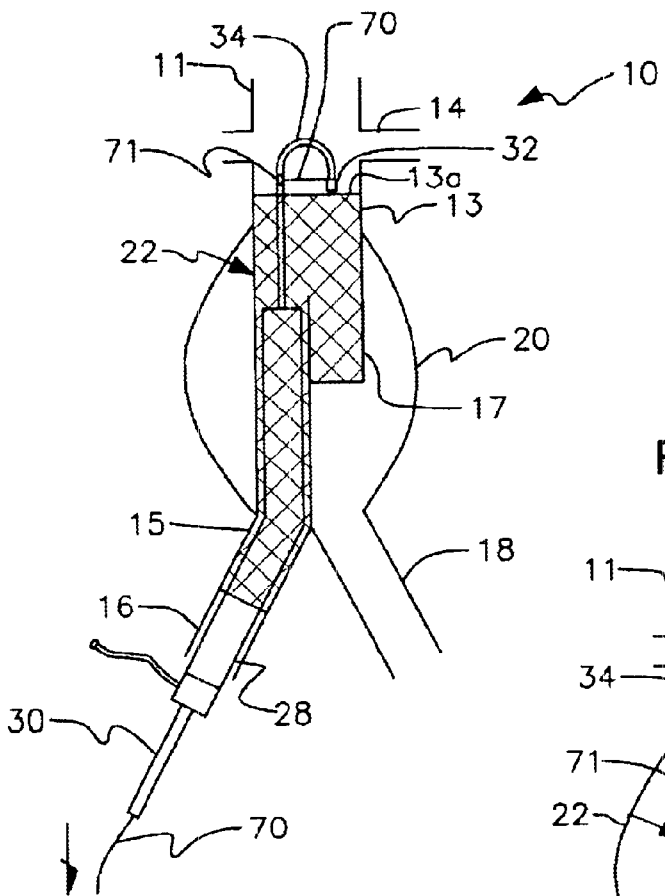
FIG. 17 is the second animation in said series.
Figure 18:
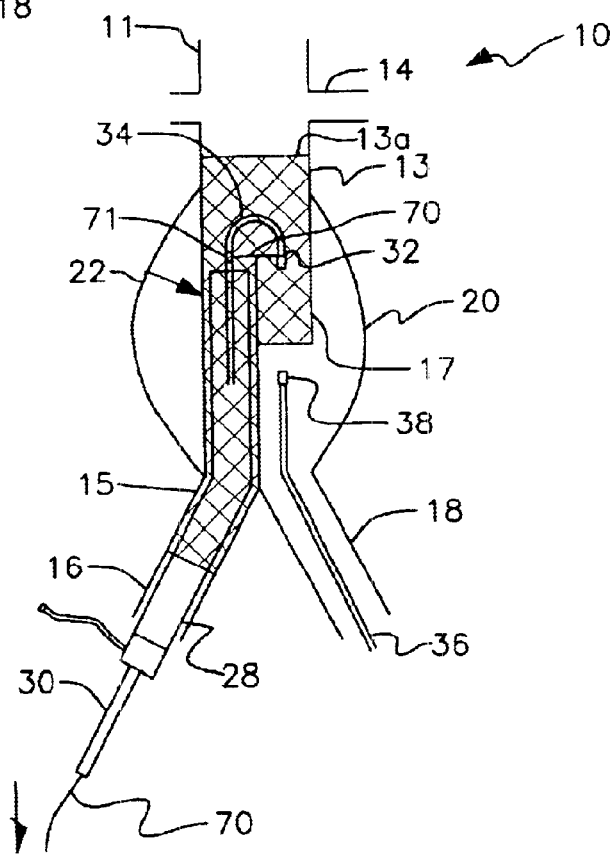
FIG. 18 is the third animation in said series.

In the alternative embodiment of FIG. 16, first catheter 30 is straight-in-configuration and has an opening 71 formed therein near its distal end. Pull string 70 is introduced into the proximal end of first catheter 30 and said pull string exits the lumen of said first catheter at said opening 71. The distal end of pull string 70 is then secured to first magnet 32, or to first catheter 30 at the base of said magnet. A return bend is therefore formed in first catheter 30 when pull string 70 is pulled from its proximal end, as indicated in FIG. 17. First catheter 30 is then pulled into waist area 13 of stent graft 22 as depicted in FIG. 18, thereby positioning said first magnet 32 into a position where it is easily engageable by second magnet 38 at the distal end of second catheter 36.

FIG. 17 depicts pull string 70 received through first catheter 30 out string aperture 71 and secured coincident to first magnet 32. Retraction of pull string 70 establishes return bend 34 as shown in FIG. 18 wherein first magnet 32 is positioned in opposing relation to second magnet 38 (FIG. 19).

Figure 19:
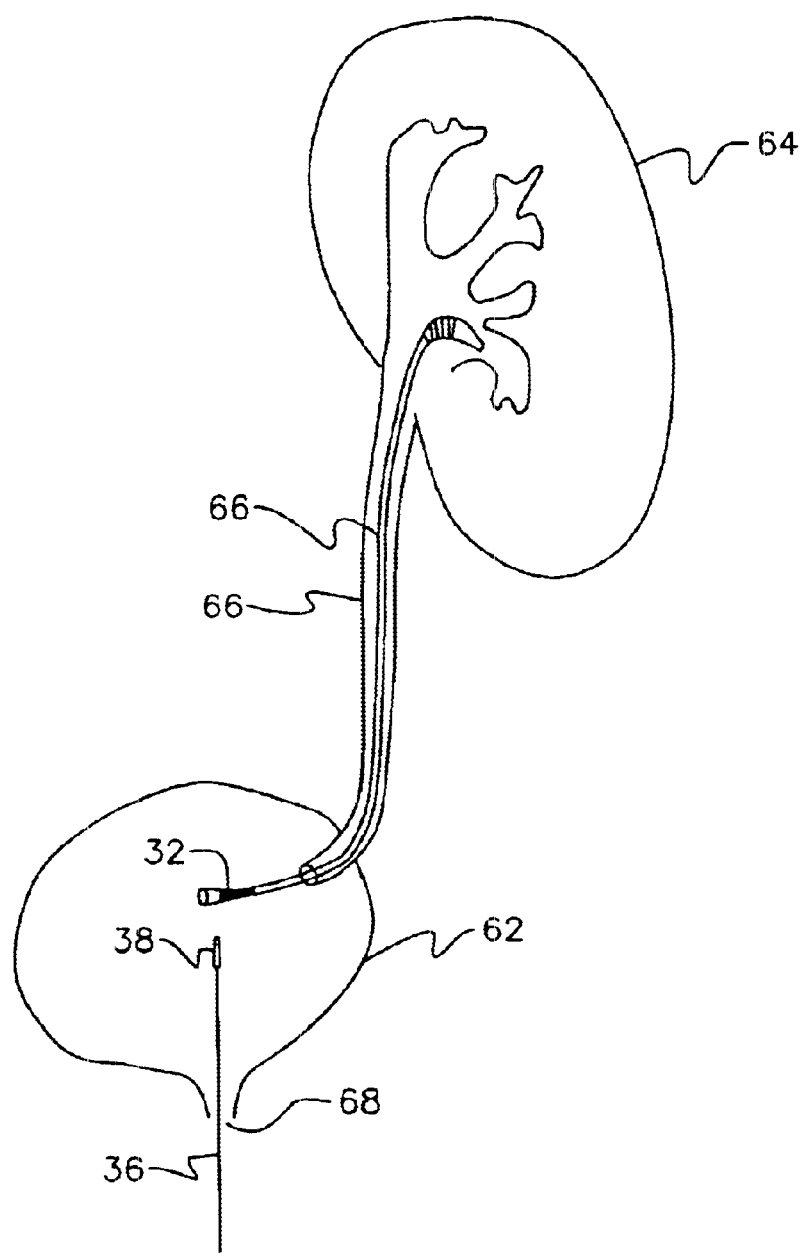
FIG. 19 is a diagrammatic view of a fourth embodiment.

A variation of the alternative embodiment is depicted in FIG. 19. Guide wire 70 exits opening 71 and is placed proximal to magnet 32 which is affixed into catheter 30 at the end of the catheter.

FIG. 19 depicts another use for magnets 32, 38. In this embodiment, magnet 32 is mounted to a first end of a nephroureteral stent 60 that extends from bladder 62 to kidney 64 through ureter 66. Magnet 38 is mounted on the distal free end of catheter 36 as in the first embodiment and is introduced into bladder 62 through urethra 68. It has an opposite polarity relative to magnet 32 and thus coupling of the magnets 32, 38 occurs when magnet 38 is brought into close proximity with magnet 32. Magnet 32 may also be provided in the form of a ferrous metal band. When the magnetic coupling has taken place, catheter 36 is withdrawn through urethra 68, pulling magnet or metal band 32 and hence nephroureteral stent 60 with it.

Having disclosed two multiple novel uses for the novel method of coupling catheters to one another by magnetic means, numerous other applications will become apparent to those skilled in the medical arts.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,
What is claimed is:

1. A method for installing a contralateral limb to a stent graft positioned in an abdominal artery to treat an aneurysm, said stent graft having an elongate leg and a truncate leg, comprising the steps of:

inserting a first guide wire through an incision endoluminally into a first common femoral artery and pushing said first guide wire into said abdominal artery until a leading end of said first guide wire extends beyond a leading end of said stent graft;

introducing a first sheath into said elongate leg of said stent graft, using said first guide wire to guide said first sheath into said elongate leg, said elongate leg having a trailing end received within said first common iliac artery; removing said first guide wire from said sheath;

providing a first catheter having a return bend formed near a distal end thereof and having a first magnet means mounted to said distal end;

introducing said first catheter into a lumen of said first sheath and pushing said first catheter until said return bend emerges from said lumen of said first sheath;

displacing said first catheter in a distal-to-proximal direction until said first magnet means emerges from said hollow interior of said stent graft and into the interior of said aneurysm;

providing a second catheter having a second magnet means on a distal free end thereof, said second magnet means having a polarity opposite to a polarity of said first magnet means;

introducing said second catheter into a second, opposite common femoral artery and positioning its distal free end near said first magnet means so that said first and second magnet means are attracted to one another and enter into magnetically coupled relation to one another;

pulling said second catheter into the hollow interior of said stent graft;

introducing a second guide wire into the lumen of said second catheter until the distal free end of said second guide wire has extended completely through second catheter and through said stent graft;

removing said first and second catheters;

introducing a second sheath over said second guide wire until the distal free end of said second sheath has entered the hollow interior of said stent graft;

introducing a contralateral limb through said second sheath until the distal free end of said contralateral limb has extended from said second sheath and entered into the hollow interior of said stent graft;

said contralateral limb deploying under its inherent bias so that it expands in diameter; and withdrawing said second sheath;

whereby blood flows into a first end of said stent graft and out the bifurcated lower end thereof into left and right iliac arteries.

2. The method of claim 1, wherein the step of removing said first and second catheters is accomplished by pulling on said second catheter until the magnetic coupling between said first and second magnet means is overcome.

3. The method of claim 1, further comprising the step of employing a deployment system to facilitate introduction of said contralateral limb through said second sheath.

4. The method of claim 1, wherein said first magnet means is a metal band formed of a ferrous material.

5. The method of claim 1, wherein said second magnet means is a metal band formed of a ferrous material.

* * * * *